(12) United States Patent
Park et al.

(10) Patent No.: US 11,564,881 B2
(45) Date of Patent: Jan. 31, 2023

(54) THERAPEUTIC AGENT TARGETING AND FIXATION MEDICAL DEVICE USING MAGNET ARRAY

(71) Applicant: INDUSTRY FOUNDATION OF CHONNAM NATIONAL UNIVERSITY, Gwangju (KR)

(72) Inventors: Jongoh Park, Gyeonggi-do (KR); Eunpyo Choi, Gwangju (KR); Chang-Sei Kim, Gwangju (KR); Byungjeon Kang, Gwangju (KR); Gwangjun Go, Gwangju (KR); Kyungmin Lee, Gwangju (KR); Jiwon Han, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 1232 days.

(21) Appl. No.: 16/015,662

(22) Filed: Jun. 22, 2018

(65) Prior Publication Data
US 2018/0369132 A1 Dec. 27, 2018

(30) Foreign Application Priority Data
Jun. 23, 2017 (KR) .................. 10-2017-0079910

(51) Int. Cl.
*A61K 9/00* (2006.01)
*A61K 41/00* (2020.01)
(Continued)

(52) U.S. Cl.
CPC .......... *A61K 9/0009* (2013.01); *A61B 5/1075* (2013.01); *A61B 34/73* (2016.02);
(Continued)

(58) Field of Classification Search
CPC ... A61B 2034/731; A61B 34/73; A61B 5/055; A61B 5/1075; A61B 6/032; A61B 6/037;
(Continued)

(56) References Cited

U.S. PATENT DOCUMENTS 9,078,932 B2 * 7/2015 Goldberg ............... A61K 35/28

FOREIGN PATENT DOCUMENTS

| KR | 10-0889006 | 3/2009 | |
|---|---|---|---|
| KR | 1020150003275 | 1/2015 | |
| WO | WO-2007125699 A1 * | 11/2007 | ............. A61B 34/73 |
| WO | WO-2013158521 A1 * | 10/2013 | ............. A61B 17/00 |

OTHER PUBLICATIONS

Nacev, Aleksander, Arash Komaee, and Azeem Sarwar. "Towards Control of Magnetic Fluids in Patients: Directing Therapeutic Nanoparticles to Disease Locations." IEEE Control Systems 32, No. 3 (May 16, 2012): 32-74. https://doi.org/10.1109/mcs.2012.2189052. (Year: 2012).*

(Continued)

*Primary Examiner* — Thaddeus B Cox
*Assistant Examiner* — Marc D. Honrath
(74) *Attorney, Agent, or Firm* — Harness, Dickey & Pierce, P.L.C.

(57) ABSTRACT

Provided is a therapeutic agent targeting and fixation medical device that precisely targets a therapeutic agent including a magnetic substance by using an optimized array of magnets in consideration of an affected area of a patient.

10 Claims, 5 Drawing Sheets

(51) Int. Cl.
*A61B 5/055* (2006.01)
*G16H 20/30* (2018.01)
*A61B 5/107* (2006.01)
*A61N 2/00* (2006.01)
*A61B 34/00* (2016.01)

(52) U.S. Cl.
CPC ............ *A61K 41/0052* (2013.01); *A61N 2/00* (2013.01); *A61B 5/055* (2013.01); *A61B 2034/731* (2016.02)

(58) Field of Classification Search
CPC .. A61K 41/0052; A61K 9/0009; A61K 9/141; A61K 9/5094; A61M 37/00; A61N 2/00; A61N 2/06; G16H 20/30
See application file for complete search history.

(56) References Cited

OTHER PUBLICATIONS

Barnsley, Lester C, Dario Carugo, and Eleanor Stride. "Optimized Shapes of Magnetic Arrays for Drug Targeting Applications." Journal of Physics D: Applied Physics 49, No. 22 (2016): 225501. https://doi.org/10.1088/0022-3727/49/22/225501. (Year: 2016).*
Barnsley, L. C., Carugo, D., & Stride, E. (2016). Optimized shapes of magnetic arrays for drug targeting applications. Journal of Physics D: Applied Physics, 49(22), 225501. https://doi.org/10.1088/0022-3727/49/22/225501 (Year: 2016).*
Nacev, A. et al., "Towards Control of Magnetic Fluids in Patients: Directing Therapeutic Nanoparticles to Disease Locations", pp. 33-74, IEEE Control Syst. Mag. (Jun. 2012).

* cited by examiner

THERAPEUTIC AGENT TARGETING AND FIXATION MEDICAL DEVICE USING MAGNET ARRAY

CROSS-REFERENCE TO RELATED APPLICATIONS

This U.S. non-provisional patent application claims priority under 35 U.S.C. § 119 of Korean Patent Application No. 10-2017-0079910, filed on Jun. 23, 2017, the entire contents of which are hereby incorporated by reference.

BACKGROUND

The present invention relates to therapeutic agent targeting using a magnet array, and more particularly, to a therapeutic agent targeting and fixation medical device using a magnet array.

A treatment method using a typical therapeutic agent has limitations such as nonselective toxicity and related side effects due to low directivity. Accordingly, researches on various therapeutic agent delivery systems have been actively performed in order to minimize side effects of the typical therapeutic agent and maximize medical effects thereof instead of developing new therapeutic agent due to a long development period and high expenses. In particular, various researches for improving the directivity of the therapeutic agent around a lesion using various magnets have been recently performed. A basic principle of the recent researches is the delivery of the therapeutic agent by using a principle in which as a magnetic substance, which is magnetized in a magnetic field, is included in or attached to the therapeutic agent, the magnetic substance, which is magnetized in a magnetic field, moves to an area having a high magnetic flux density. However, most of typical researches use a single superconductor magnet or permanent magnet, which has an extremely great magnetic flux density, to simply maximize an attractive force toward the magnet, thereby delivering the therapeutic agent including the magnetic substance. Since the above-described typical researches do not consider a therapeutic environment such as the kind and position of an affected area and the object of the treatment, the researches are difficult to be applied to various procedural settings, and the therapeutic agent is difficult to be exactly targeted to the affected area. In relation to this, Korean Patent Registration No. 0889006 discloses a magnetic field treatment device of a low frequency rotary permanent magnetic substance.

SUMMARY

However, since the above related art does not consider optimized arrangement and array on an affected area, such as distribution of magnets, the number of magnets, and magnetization of the magnet for an affected area, targeting of a therapeutic agent for the affected area or fixation of the targeted therapeutic agent on the affected area are inappropriately performed.

The present invention provides a therapeutic agent targeting and fixation medical device that precisely targets the therapeutic agent to the affected area by using an optimized magnet array in consideration of the affected area of a patient to resolve the aforesaid limitations. However, this may be merely illustrative, and thus the present disclosure is not limited thereto.

An aspect of the present invention provides a method for moving a magnetic substance to a desired position in a three-dimensional space, the method including: determining a stacking point, on which a magnetic substance including magnetic nanoparticles is stacked, and a target point, to which the magnetic substance moves, in a three-dimensional space; stacking the magnetic substance on the stacking point; and arranging a plurality of magnets in a space surrounding the stacking point and the target point. Here, an attractive force or a repulsive force is generated by the magnet in such a manner that the attractive force is formed in a direction in which the magnet is arranged when the stacking point is disposed between a field free point, at which a magnetic flux density is deleted by overlapping magnetic fields generated from the arranged plurality of magnets, and an arrangement point, at which the magnet is arranged, and the repulsive force is generated in a direction opposite to the direction in which the magnet is arranged when the stacking point passes the field free point from the magnet arrangement point.

Another aspect of the present invention provides a method of manufacturing a medical device for targeting and fixing a therapeutic agent including a magnetic substance to an affected area by using an array of a plurality of magnets, the method including: acquiring a 3-D medical image of an affected area of a patient by using an imaging device; extracting the affected area and setting a treatment region in order to measure a shape, size, and position of the affected area; designing a patient-specific medical device for targeting and fixing a therapeutic agent including a magnetic substance in order to design the distribution, number, and magnetization direction of the magnets on the basis of the 3-D medical image acquired from the patient; and manufacturing a fixation medical device so as to determine a shape of the fixation medical device on the basis of the design information.

Another aspect of the present invention provides a medical device for targeting and fixing a therapeutic agent including a magnetic substance to an affected area by using an array of a plurality of magnets.

Another aspect of the present invention provides a medical kit for magnet-based affected area treatment including a medical device for targeting and fixing a therapeutic agent including a magnetic substance to an affected area by using an array of a plurality of magnet and the therapeutic agent including a magnetic substance.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Definition of Terms

Figure 1:
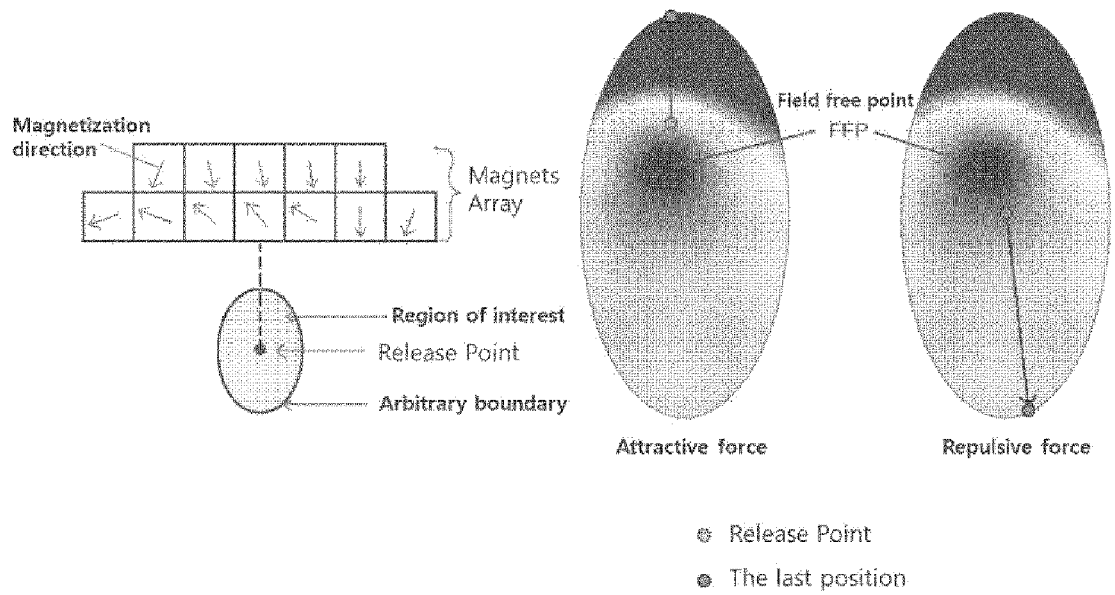
FIG. 1 is a schematic diagram illustrating a patient-specific therapeutic agent targeting and fixation medical device using an optimized array of magnets.

The term "magnetic field" as used herein refers to a magnetic flux and represents a space, in which lines of magnetic force are provided, i.e., a magnetic effect is affected like surroundings of a current or a magnet and the surface of the earth.

The term "attractive force" as used herein refers to a pulling force between two objects, which is an opposite concept of a repulsive force. When a magnet approaches an iron piece, the attractive force acts therebetween to pull each other, and rain drops fall down from the sky because the earth pulls the raindrops. As described above, various kinds of attractive forces exist in nature. A representative example is universal gravitation, which universally acts between all kinds of objects, and gravity, which acts between the earth and an object, is a kind of universal gravitation. Also, a magnetic force between S pole and N pole and an electric force between a positive charge and a negative charge are the attractive force. Furthermore, a nuclear force, which couples a proton and a neutron in an atomic nucleus, and a van der Waals force, which acts between molecules that are electrically neutral, are also the attractive force.

The term "repulsive force" used herein refers to a pushing force between two objects, which is an opposite concept of the attractive force. When S pole of one magnet approaches S pole of another magnet or N pole of one magnet approaches N pole of another magnet between two magnets, the repulsive force may be generated. Also, the repulsive force exists between electric charges having the same sign, e.g., between positive charges or between negative charges. Like the attractive force, the repulsive force of an electromagnetic force is in inverse proportion to a squared distance between two objects. That is, when a distance between two objects becomes double, a magnitude of the repulsive force decreases into a quarter, and when the distance decreases into a half, the magnitude increases four times.

The term "magnetic flux density" used herein refers to a magnetic flux per unit area in terms of a plane perpendicular to a magnetic field at one point of the magnetic field. The magnetic flux density may be referred to as magnetic induction or self-induction.

The term "patient-specific" used herein refers to a process, in which, when a 3-D medical image of an affected area of a patient is acquired by using an imaging device, and the shape, size, and position of the affected area exactly measured to set affected area extraction and a treatment region during manufacturing a fixation medical device according to the present invention, a constitution of a therapeutic agent is determined according to the position, size, and state of the affected area, the therapeutic agent is prepared by including all of or selectively including some of a medicine, a magnetic material, or a cell for treatment in a biocompatible/biodegradable polymer structure, and the shape of the fixation medical device is determined as, e.g., a detachable-type or a fixed-type on the basis of the 3-D medical image.

DETAILED DESCRIPTION

An aspect of the present invention, the provided is a method for moving a magnetic substance to a desired position in a three-dimensional space, the method including: determining a stacking point, on which a magnetic substance including magnetic nanoparticles is stacked, and a target point, to which the magnetic substance moves, in a three-dimensional space; stacking the magnetic substance on the stacking point; and arranging a plurality of magnets in a space surrounding the stacking point and the target point. Here, an attractive force or a repulsive force is generated by the magnet in such a manner that the attractive force is formed in a direction in which the magnet is arranged when the stacking point is disposed between a field free point, at which a magnetic flux density is deleted by overlapping magnetic fields generated from the arranged plurality of magnets, and an arrangement point, at which the magnet is arranged, and the repulsive force is generated in a direction opposite to the direction in which the magnet is arranged when the stacking point passes the field free point from the magnet arrangement point.

In the above method, the magnetic nanoparticles may include magnetite or maghemite, and the magnet may include a permanent magnet, soft ferrite, ferrite, neodymium, Alico, samarium cobalt, or a rubber magnet.

Another aspect of the present invention, the provided is a method of manufacturing a medical device for targeting and fixing a therapeutic agent including a magnetic substance to an affected area by using an array of a plurality of magnets, the method including: acquiring a 3-D medical image of an affected area of a patient by using an imaging device; extracting the affected area and setting a treatment region in order to measure a shape, size, and position of the affected area; designing a patient-specific medical device for targeting and fixing a therapeutic agent including a magnetic substance in order to design the distribution, number, and magnetization direction of the magnets on the basis of the 3-D medical image acquired from the patient; and manufacturing a fixation medical device so as to determine a shape of the fixation medical device on the basis of the design information.

In the above manufacturing method, the designing of a medical device for targeting and fixing a therapeutic agent may include: setting initial values of a maximum magnet array range, the number of magnets to be used, and an initial magnet magnetization direction; calculating an initial magnetic force in a specific direction at a point of interest (POI); changing the magnet magnetization direction to determine a magnetic force and a magnetization direction so that the calculated magnetic force has a maximum value; comparing a magnitude of a magnetic force in a previous process with that of a magnetic force in a current process; checking the number of magnets to be used; and finally arranging the magnets on the basis of the determined magnet magnetization direction.

In the above manufacturing method, the image device may include X-ray, CT, PET, or MRI, and the fixation medical device may be a detachable-type or a fixed-type.

In the above manufacturing method, the therapeutic agent including the magnetic substance may include a medicine including or attached with magnetic nanoparticles, a cell therapeutic agent, or a mixture thereof, and the cell therapeutic agent may include a mesenchymal cell, a cartilage cell, a bone cell, a neural stem cell, a stem cell, or an immune cell.

Another aspect of the present invention, the provided is a medical device for targeting and fixing a therapeutic agent including a magnetic substance to an affected area by using an array of a plurality of magnets Another aspect of the present invention, the provided is a medical kit for magnet-based affected area treatment including a medical device for targeting and fixing a therapeutic agent including a magnetic substance to an affected area by using an array of a plurality of magnet and the therapeutic agent including a magnetic substance.

In the medical kit, the therapeutic agent including a magnetic substance may include a medicine including or attached with magnetic nanoparticles, a cell therapeutic agent, or a mixture thereof, and the cell therapeutic agent may include a mesenchymal cell, a cartilage cell, a bone cell, a neural stem cell, a stem cell, or an immune cell.

Hereinafter, specific embodiments will be described in detail with reference to the accompanying drawings.

The present invention may, however, be embodied in many different forms and should not be construed as being limited to the embodiments set forth herein; rather, these embodiments are provided so that those skilled in the art thoroughly understand the present invention. Rather, these embodiments are provided so that this disclosure will be thorough and complete, and will fully convey the scope of the present disclosure to those skilled in the art. Also, in the figures, a thickness or dimension of each of layers is exaggerated for clarity of illustration.

It will be understood that it is referred to as being "on," "connected to", "stacked", or "coupled to" another element, it may be directly on, connected, stacked, or coupled to the other element or intervening elements may be present. In contrast, when an element is referred to as being "directly on," "directly connected to" or "directly coupled to" another element or layer, there are no intervening elements or layers present. Like reference numerals refer to like elements throughout. As used herein, the term "and/or" includes any and all combinations of one or more of the associated listed items.

As used herein, terms such as "first," "second," etc. are used to describe various members, components, regions, layers, and/or portions. However, it is obvious that the members, components, regions, layers, and/or portions should not be defined by these terms. The terms do not mean a particular order, up and down, or superiority, and are used only for distinguishing one member, component, region, layer, or portion from another member, component, region, layer, or portion. Thus, a first member, component, region, layer, or portion which will be described may also refer to a second member, component, region, layer, or portion, without departing from the teaching of the present invention.

Spatially relative terms, such as "above" or "upper" and "below" or "lower" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the exemplary term "above" may encompass both an orientation of above and below. The device may be otherwise oriented (rotated 90 degrees or at other orientations) and the spatially relative descriptors used herein interpreted accordingly.

The terms used herein are for illustrative purposes of the present invention only and should not be construed to limit the meaning or the scope of the present invention. As used in this specification, a singular form may, unless definitely indicating a particular case in terms of the context, include a plural form. Also, the expressions "comprise" and/or "comprising" used in this specification neither define the mentioned shapes, numbers, steps, operations, members, elements, and/or groups of these, nor exclude the presence or addition of one or more other different shapes, numbers, steps, operations, members, elements, and/or groups of these, or addition of these. The term "and/or" used herein includes any and all combinations of one or more of the associated listed items.

Additionally, the embodiment in the detailed description will be described with sectional views as ideal exemplary views of the inventive concept. In the drawings, for example, according to the manufacturing technology and/or tolerance, the modification of the illustrated shape may be expected. Thus, the exemplary embodiments of the present disclosure must not be interpreted to be limited by a particular shape that is illustrated in the drawings and must include a change in the shape occurring, for example, during manufacturing.

Hereinafter, the present invention will be described in more detail through embodiments. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art.

FIG. 1 is a schematic diagram illustrating a method of delivering a magnetic substance to a desired position in a three-dimensional space by using a magnet array according to an embodiment of the present invention. In FIG. 1, a rectangle represents an arbitrary magnet, and a blue point represents a release point at which a therapeutic agent (medicine, cell therapeutic agent, and medicine+therapeutic agent) including or attached with a magnetic substance (which is reacts to a magnetic field) is released. To achieve the technical object of the present invention, two or more magnets may be arranged as in FIG. 1, and a magnetic force acting on the therapeutic agent at a region of interest (ROI) and a point of interest (POI) may be used.

The patient-specific therapeutic agent targeting according to the present invention may generate and use a force (pushing force, repulsive force), which acts to move away from the magnet, and a force (pulling force, attractive force), which acts to move adjacent to the magnet, by using two or more magnets. A basic driving principle for the therapeutic agent targeting is as stated below. The therapeutic agent including or attached with the magnetic substance moves to a region having a great magnetic flux density in a space that is affected by a magnetic field. Accordingly, when only one magnet is used like the method of the typical researches, gradient of the magnetic flux density in ROI is always high at a portion adjacent to the magnet. Thus, the therapeutic agent including or attached with the magnetic substance is always attracted toward a portion at which the magnet is disposed. However, as a point FFP (a field free point, at which the magnetic flux density is deleted by overlapping magnetic fields of two or more magnets), at which the magnetic flux density becomes zero, is generate, and a point, at which the therapeutic agent including the magnetic substance is released, is set at each of the front and rear portions with reference to the point, at which the magnetic field is deleted and removed, through an optimized arrangement by using two or more magnets according to the sex and age of the patient, the kind and position of the affected area, and the object of treatment, the patient-specific therapeutic agent targeting according to the present invention may use an attractive force, which pulls the therapeutic agent, and a repulsive force, which pushes the therapeutic agent, in order to target and fix the therapeutic agent to the affected area. In other words, when the release point of the therapeutic agent is positioned between the FFP, at which the magnetic flux density is deleted, and an arrangement point of the magnet, the therapeutic agent is pulled toward a portion having the high magnetic flux density, i.e., the arrangement point of the magnet (attractive action). Also, when the therapeutic agent is released at a point, which passes the FFP from the arrangement point of the magnet, the therapeutic agent is pushed away from the portion having the high magnetic flux density, i.e., the arrangement point of the magnet (repulsive action). On the basis of the above-described principle, a minimum vertical distance from the release point of the therapeutic agent to the surface of the magnet, the region of interest, in which a force acts, the distribution of magnets, the number of magnets, the magnetization change angle, the kind of magnets may be adjusted according to the kind and position of the affected area and the object of treatment. Also, while the above-described conditions are satisfied, the arrangement having the maximum force in the direction toward or away from the magnet may be optimized and used. Through the above-described optimization, the therapeutic agent including or attached with the magnetic substance may be exactly targeted and fixed to the affected area, thereby maximizing treatment effects.

Here, the therapeutic agent including or attached with the magnetic substance, in consideration of the optimized treatment effects, may include a medicine, a cell therapeutic agent, or a mixture thereof, or a magnetic material or nanoparticles, which contains a pharmacologically active constituent. The magnetic substance may include magnetite or maghemite, and the magnet may include a permanent magnet, soft ferrite, ferrite, neodymium, Alico, samarium cobalt, or a rubber magnet.

Figure 2:
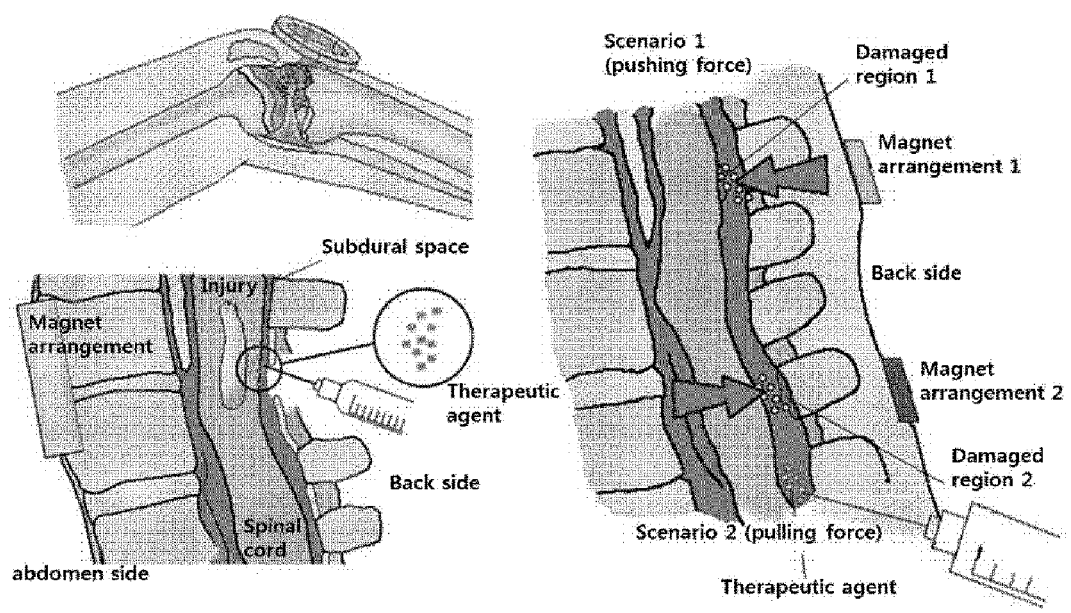
FIG. 2 is a schematic diagram illustrating an application example of the patient-specific therapeutic agent targeting and fixation medical device according to the present invention.

FIG. 2 is a schematic diagram illustrating the patient-specific therapeutic agent targeting and fixation medical device, which precisely targets the therapeutic agent to the affected area by using the optimized arrangement in consideration of the affected area of the patient on the basis of the method in FIG. 1. As illustrated in FIG. 2, in case of treatment of injuries on a general cartilage or spinal cord and spine, the therapeutic agent may be concentrated on the affected area by using the repulsive force or the attractive force, which is generated by the magnet arrangement, in consideration of the position of the affected area and the position of injecting the therapeutic agent by using the arrangement of two or more magnets. Also, when the therapeutic agent may not be injected adjacent to the affected area due to restrictions such as a safety reason around the affected area or a structural limitation of a body, as the magnets are arranged to have directivity, the therapeutic agent may be delivered and exactly targeted to the target affected area. Although an embodiment for a specific application field is provided in FIG. 2 in order to easily explain the concept of the patient-specific therapeutic agent targeting and fixation medical device according to the present invention, the embodiment of the present invention is not limited to the treatment of injuries on cartilage or spinal cord and spine. For example, the therapeutic agent targeting and fixation medical device may be applied to various fields, which may target the therapeutic agent to the affected area to treat the same, such as intravenous injection. Also, the therapeutic agent targeting and fixation medical device may be used as a therapeutic agent fixation device, which holds the therapeutic agent not to be escaped from the affected area by using an external device (e.g., targeting through the electromagnetic field, injection adjacent to the affected area by using a catheter or a needle) after the therapeutic agent is targeted to the affected area.

Figure 3:
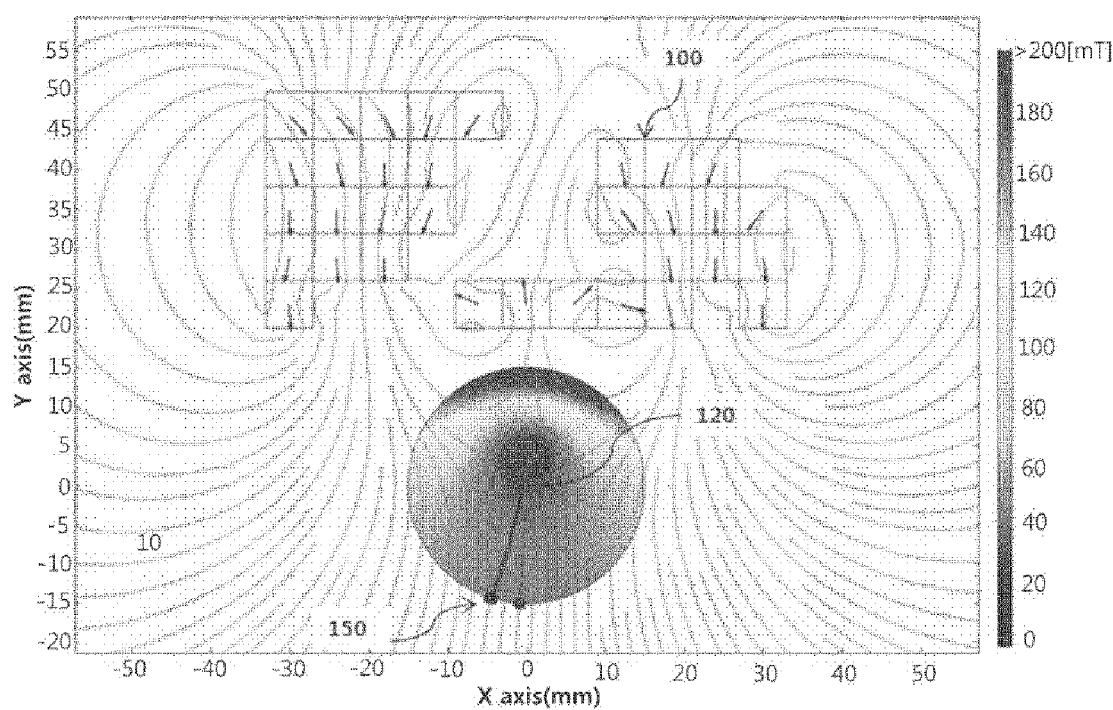
FIG. 3 is a graph illustrating a simulation in which a therapeutic agent including the magnetic substance moves away from a position at which the magnet is arranged by a repulsive force on a two-dimensional plane.

FIG. 3 is a graph illustrating a simulation in which the therapeutic agent including the magnetic substance moves away from the point, at which the magnet is arranged, by the generated repulsive force on a two-dimensional plane. As illustrated in FIG. 3, the therapeutic agent including a magnetic substance 150 moves further away from a release point 120 by the repulsive force generated by a permanent magnet 100. The simulation result is obtained through the optimization design by assuming that the position of the affected area of the patient is positioned further away from the arrangement point of the permanent magnet 100 than the release point 120, at which the therapeutic agent is released. In particular, the movement direction and speed of the therapeutic agent may be adjusted according to a distance between the release point 120 of the therapeutic agent and the arrangement point of the permanent magnet 100, the region of interest, in which a force acts, the distribution of magnets, the number of magnets, a magnetization change angle, the kinds of magnets, properties of magnets, and properties of the therapeutic agent. Thus, the device enabling the therapeutic agent to move away from the magnet through arrangement of two or more magnets may be designed.

Figure 4:
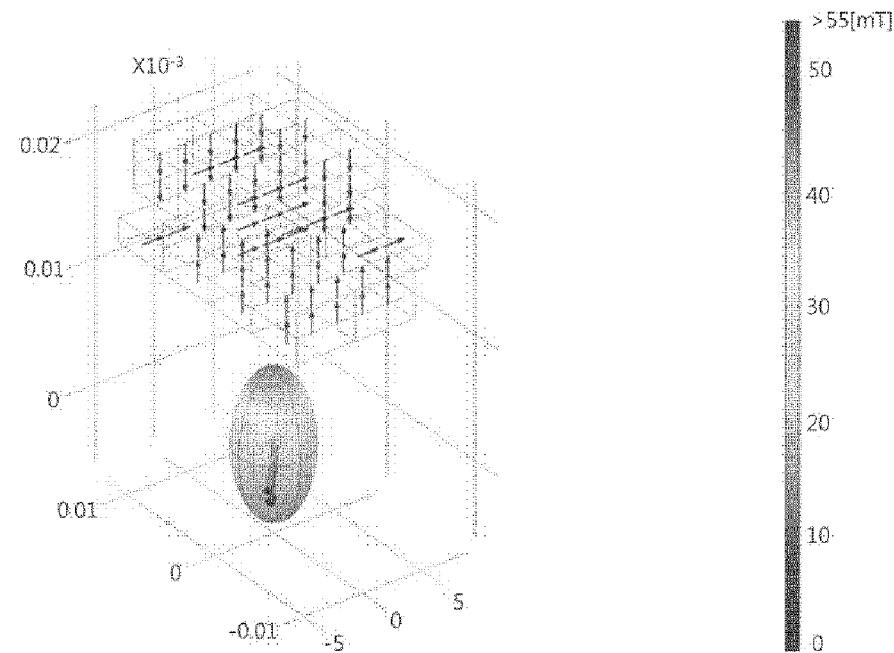
FIG. 4 is a graph illustrating a simulation in which an optimized method performed in FIG. 3 is performed in a three-dimension.

FIG. 4 is a graph illustrating a simulation in which the optimization method performed in FIG. 3 may be performed in three-dimension. The distance between the release point 120 of the therapeutic agent used in the above simulation and the arrangement point of the permanent magnet 100, the region of interest in which a force acts, the distribution of magnets, the number of magnets, the magnetization change angle, the kinds of magnets, the properties of magnets, and the properties of the therapeutic agent are arbitrarily set. Also, only an operation moving away in a Z-axial (vertical) direction is realized in order to show that the therapeutic agent including the magnetic substance 150 may move away from the magnet, and a direction with respect to X and Y axes (i.e., arbitrary three-dimensional direction) may be designed appropriately to the position of the specific affected area and the environment and the object of the procedure.

Figure 5:
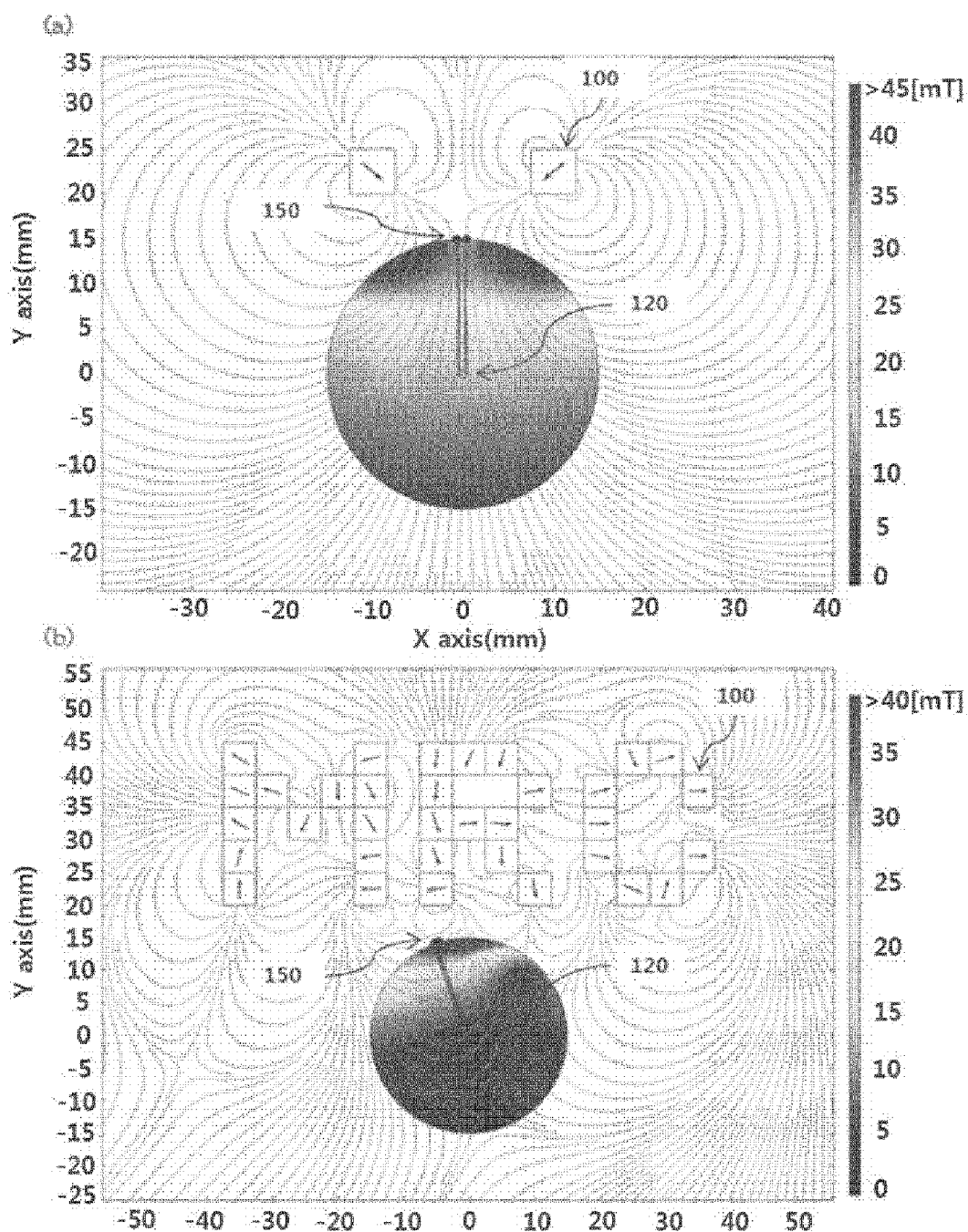
FIG. 5 is a graph illustrating a simulation in which a therapeutic agent including a magnetic substance is pulled to a position at which a magnet is arranged by an attractive force on a two-dimensional plane.

FIG. 5 is a graph illustrating a simulation in which the therapeutic agent including the magnetic substance 150 is pulled in a direction toward the arrangement point of the permanent magnet 100 by the generated attractive force on a two-dimensional plane. FIG. 5A shows a result of a simulation in which, like the phenomenon in which the therapeutic agent including the magnetic substance is pulled toward the magnet when one magnet is disposed in a direction perpendicular to the release point 120, the therapeutic agent is pulled in the same path through an array of two permanent magnets 100. This represents that the therapeutic agent may perpendicularly move in a desired direction by using a different arrangement even when the permanent magnet 100 may not be perpendicularly arranged according to circumstances (specific affected area position or specific body structure). FIG. 5B illustrates a state in which the arrangement of magnets is firstly determined appropriately to the number of magnets and a usage object, and then the magnetization angle is optimized to have a maximum force, so that the magnet may be used appropriately to the purpose. The above result also represents that the attractive force and the repulsive force, which are generated by the magnet, may be freely adjusted.

Figure 6:
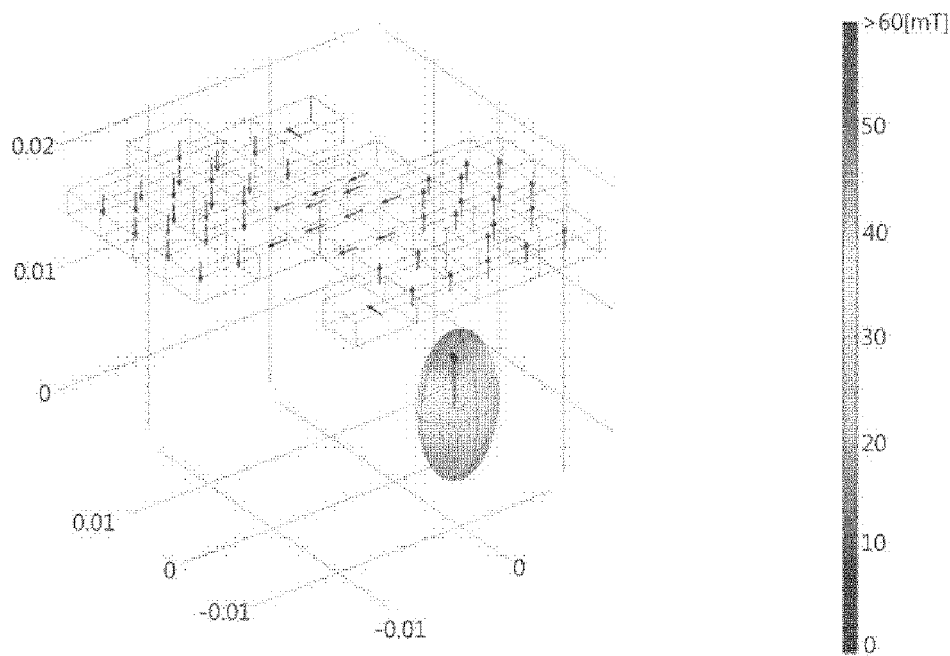
FIG. 6 is a graph illustrating a simulation in which an optimization method realized in FIG. 5 is performed in a three-dimension.

FIG. 6 is a graph illustrating a simulation in which the optimization method realized in FIG. 5 is performed in a three-dimension. As illustrated, although a direction in which the magnet moves is arbitrarily illustrated as the Z-axis (vertical direction) in order to easily explain the technical concept of the present invention in FIG. 6, the movement direction of the magnet may have a specific directivity in an arbitrary three-dimensional space according to the properties of the magnet and the properties of the therapeutic agent.

Figure 7:
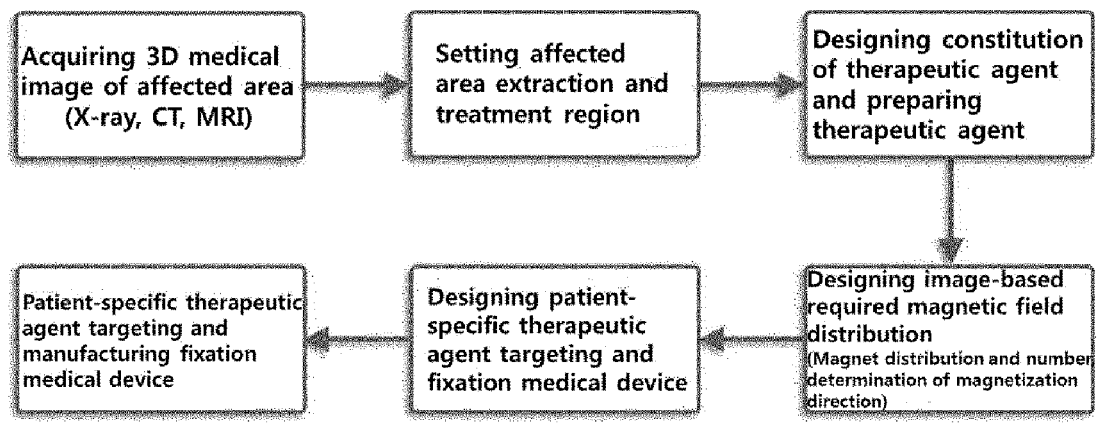
FIG. 7 is a process chart illustrating a process of manufacturing a patient-specific therapeutic agent targeting and fixation medical device according to the present invention.

FIG. 7 is a process chart showing a manufacturing process of the fixation medical device applied with a technology for exactly targeting the therapeutic agent to the affected area by using the optimized arrangement of the magnet in consideration of the affected area of the patient. The above-described manufacturing process includes six steps. Firstly, a 3-D medical image of the affected area of the patient is acquired through an imaging device such as X-ray, CT, or MRI, and then the shape, size, and position of the affected area are exactly measured to set affected area extraction and treatment region. Thereafter, a step of therapeutic agent constitution design and preparation is provided. Here, the constitution of the therapeutic agent may be determined according to the position, size, and state of the affected area, and the therapeutic agent may be prepared by including all of or selectively including some of a medicine, a magnetic material, or a cell for treatment in a biocompatible/biodegradable polymer structure. For example, the therapeutic agent coupled to the magnetic material may be prepared and injected to the cell for treatment. Thereafter, an image-based required magnetic field distribution design for exactly targeting the prepared therapeutic agent to the affected area on the basis of the 3-D medical image acquired from the patient is performed. This represents a process in which the distribution of magnets, the number of magnets, and the magnetization direction, which are optimized to generate the magnetic field of the patient-specific therapeutic targeting and fixation medical device according to the present invention, thereby exactly inducing the therapeutic agent to the affected area by the magnetic material. In order to be manufactured in the patient-specific type, the number and distribution of magnets and the magnetization direction are determined in consideration of the position and size of the affected area through the previously measured 3-D medical image of the affected area of the patient, and then, on the basis of the above information, the shape of the fixation medical device is determined into the detachable-type or the fixed-type, thereby performing the specific design and manufacturing process on the basis of the determined type.

Figure 8:
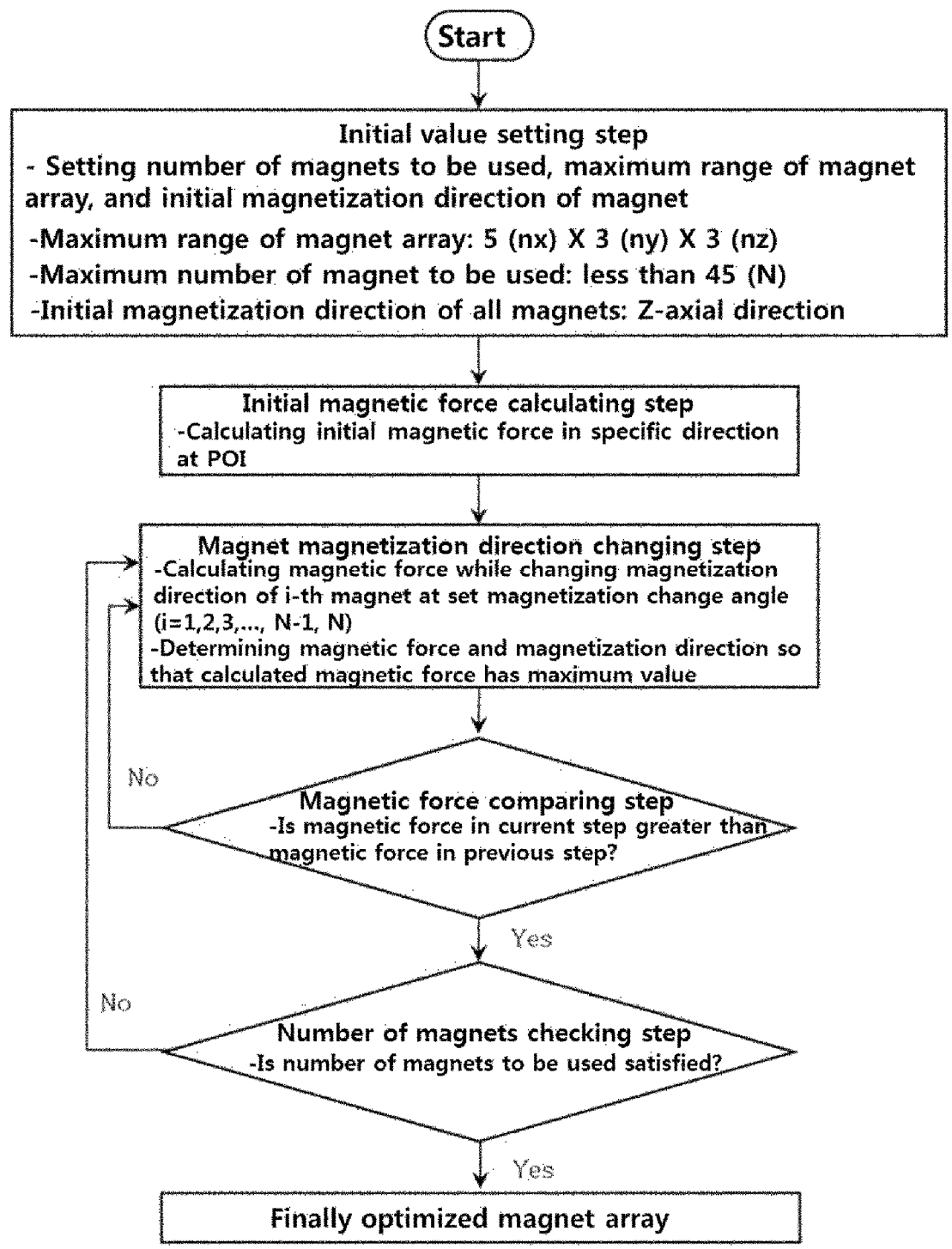
FIG. 8 is a flowchart illustrating a magnet array optimization for an image-based magnetic field distribution design during the manufacturing process in FIG. 7.

FIG. 8 is a flowchart illustrating the optimization of the magnet array for the image-based magnetic field distribution design after conditions of the affected area extracting and the treatment region and conditions of the therapeutic agent are determined during the process of manufacturing the patient-specific therapeutic agent targeting and fixation medical device according to the present invention. Firstly, as an initial value setting step for the optimized magnet array according to the determined conditions (e.g., the treatment region and position, and the therapeutic agent), the maximum range of the magnet array, the number of magnets to be used, and the magnetization direction of the initial magnet are set. Here, the maximum range of the magnet array is set wider than the range of the number of magnets to be used, and the magnetization directions of all initial magnets are set to the same direction. Thereafter, as an initial magnetic force calculation step, a magnetic force acting on the therapeutic agent in a specific direction (i.e., affected area position) at the release point, at which the therapeutic agent is released, on the based of the initially set magnet array is calculated. This is to deduce an optimized force by comparing the calculated existing magnetic force acting on the therapeutic agent with the magnetic force acting on the therapeutic agent, which is newly calculated according to the magnetization direction change. Thereafter, in a step of changing the magnetization direction of the magnet, a univariate search of a direct method is applied as an example. According to the method, magnets are numbered from 1 to N, and then a magnetization angle of the 1-st magnet is changed into a set magnetization change angle (360°/set magnetization change angle). Here, the force at POI s calculated whenever the magnetization angle of the 1-st magnet is changed, and a maximum force among the calculated forces is stored to store the magnetization direction as the magnetization direction of the 1-st magnet. The above process is repeated upto the N-th magnet, and then the magnetization direction when a maximum force is generated is set to each magnet. Also, a process of deleting the magnet having the corresponding number, when a force is not affected even when the magnetization direction is changed, is repeated until the number of magnets to be used is satisfied. Finally, an optimized force, when all conditions are satisfied, is stored, and the magnetization direction of each magnet is stored, so that the stored information is applied to the design and manufacturing of the patient-specific therapeutic agent targeting and fixation device.

As a result, since the patient-specific therapeutic agent targeting and fixation medical device according to the present invention may generate, maximize, and, furthermore, freely adjust the repulsive force and the attractive force of the magnet in consideration of the optimized arrangement and array for the distribution of two or more magnets, the number of magnets, and the magnetization direction of the magnet, the therapeutic agent may be precisely targeted and fixed according to the kind and position of the affected area and the object of treatment, and thus the effective treatment effects may be anticipated.

According to an embodiment of the present invention, the production effect of the patient-specific therapeutic agent targeting and fixation medical device, which precisely targets the therapeutic agent to the affected area by using the optimized array of the magnets in consideration of the affected area of the patient, may be realized. However, the scope of the present invention is not limited to such an effect.

Accordingly, a person having ordinary skill in the art will understand from the above that various modifications and other equivalent embodiments are also possible. Hence, the real protective scope of the present invention shall be determined by the technical scope of the accompanying Claims.

What is claimed is:

1. A method of manufacturing a medical device for targeting and fixing a therapeutic agent comprising a magnetic substance to an affected area by using an array of a plurality of magnets, the method comprising:

acquiring a 3-D medical image of the affected area of a patient by using an imaging device;

extracting the affected area and setting a treatment region in order to measure a shape, a size, and a position of the affected area;

designing a patient-specific medical device for targeting and fixing the therapeutic agent comprising the magnetic substance in order to design a distribution, a number, and a magnetization direction of the magnets on a basis of the 3-D medical image acquired from the patient, wherein the plurality of magnets are arranged in a space surrounding a stacking point and/or a target point, and wherein the plurality of magnets delete a magnetic flux density by overlapping magnetic fields; and manufacturing a magnet arrangement device for attaching around the affected area so as to determine a shape of the magnet arrangement device on the basis of the distribution, number, and magnetization direction of the magnets.

2. The method of claim 1, wherein the designing of a medical device for targeting and fixing a therapeutic agent comprises:

setting initial values of a maximum magnet array range, the number of magnets to be used, and an initial magnet magnetization direction;

calculating an initial magnetic force in a specific direction at a point of interest (POI);

changing the magnet magnetization direction to determine a magnetic force and a magnetization direction so that the calculated magnetic force has a maximum value;

comparing a magnitude of a magnetic force in a previous process with that of a magnetic force in a current process;

checking the number of magnets to be used; and arranging the magnets on the basis of the determined magnet magnetization direction.

3. The method of claim 1, wherein the imaging device comprises X-ray, CT, PET, or MRI.

4. The method of claim 1, wherein the magnet arrangement device is a detachable-type or a fixed-type.

5. The method of claim 1, wherein the therapeutic agent comprising the magnetic substance comprises a medicine comprised of or attached with magnetic nanoparticles, a cell therapeutic agent, or a mixture thereof.

6. The method of claim 5, wherein the cell therapeutic agent comprises a mesenchymal cell, a cartilage cell, a bone cell, a neural stem cell, a stem cell, or an immune cell.

7. A medical device for targeting and fixing the therapeutic agent comprising the magnetic substance to the affected area by using the array of the plurality of magnets, wherein the medical device is manufactured by the method of claim 1.

8. A medical kit for magnet-based affected area treatment comprising the medical device for targeting and fixing the therapeutic agent comprising the magnetic substance to the affected area by using the array of the plurality of magnet of claim 7 and the therapeutic agent comprising the magnetic substance.

9. The medical kit of claim 8, wherein the therapeutic agent comprising the magnetic substance comprises a medicine comprised of or attached with magnetic nanoparticles, a cell therapeutic agent, or a mixture thereof.

10. The medical kit of claim 9, wherein the cell therapeutic agent comprises a mesenchymal cell, a cartilage cell, a bone cell, a neural stem cell, a stem cell, or an immune cell.

* * * * *